United States Patent [19]

Chang et al.

[11] Patent Number: 5,063,244

[45] Date of Patent: Nov. 5, 1991

[54] PROCESS FOR THE ISOLATION OF ANTIFUNGAL AGENTS (5-METHOXY-7-HYDROXYFLAVAN) FROM DRAGON'S BLOOD RESIN AND ITS USE IN AGRICULTURE

[75] Inventors: Ming-Ju Chang; Yuan-Hsun Hsu; Mei-Hui Kuo; Tai-Sen Soong, all of Taipei, Taiwan

[73] Assignee: Development Center for Biotechnology, Taiwan, Taiwan

[21] Appl. No.: 559,079

[22] Filed: Jul. 30, 1990

[51] Int. Cl.$^5$ .............................................. A01N 43/16
[52] U.S. Cl. ..................................................... 514/456
[58] Field of Search ........................................ 514/456

[56] References Cited

FOREIGN PATENT DOCUMENTS 0004579 10/1979 European Pat. Off. ............ 514/456

OTHER PUBLICATIONS

Okamoto et al.; C.A. vol. 105 (1986) 94525M.
Olaniyi et al.; C.A. vol. 78(1973) 58277X
Cardillo et al.; vol. 76 (1972) 56573a.

Primary Examiner—Allen J. Robinson
Attorney, Agent, or Firm—Birch, Stewart, Kolasch & Birch

[57] ABSTRACT

5-methoxy-7-hydroxyflavan (compound (I) was isolated and purified from Dragon's Blood resin. The purification process involves 50% ethanol soxhletion overnight and then fraction through silica column with a series of solvent elution. The purified compound (I) was crystallized in benzene: hexane (1:1). The pure compound was identified by instruments including IR, NMR, FAB-MS, and GC-MS and acetylation reaction to confirm the structure. This compound was found to be a strong antifungal chemical with broad spectra against *Fusarium oxysporium fsp. niveum, Phytophora capsici, Phoma asparagi, Pythium spinosum, Pythium aphanidermatum, Phthium sylvaticum, Sclerotium rolfsii,* and *Sclerotinia sclerotiorum*. For whole plant in vivo testes, it was found that compound (I) significantly protected mung bean and cabbage from being infested and damaged by *Sclerotium rolfsii* and *Pythium aphanidermatum* respectively. Toxicology experiments with compound (I), it shown no toxcity or effect to animals by peroral 300 mg/kg or intraperitoneal 100 mg/kg (by Brion Research Institute of Taiwan). It is a definite conclusion that compound is a safe fungicide in agriculture.

2 Claims, 6 Drawing Sheets

PROCESS FOR THE ISOLATION OF ANTIFUNGAL AGENTS (5-METHOXY-7-HYDROXYFLAVAN) FROM DRAGON'S BLOOD RESIN AND ITS USE IN AGRICULTURE

FIELD OF THE INVENTION

The present invention relates to a process for the isolation of antifungal agent (5-methoxy-7-hydroxyflavan) from Dragon's Blood resin and its use in agriculture.

BACKGROUND OF THE INVENTION

Fungal pathogens, especially most of the soil-borne, cause severe damage in productions. Most chemical fungicides used today are carcinogenic to humans and pollute our environments. The urgency of searching and developing safe, potent and bio-degradable fungicides for agriculture is apparent. Plant materials are natural sources for the antifungal compounds and a screening program has been established to search for the potential compounds.

Dragons's Blood is a commercially available resin, principly derived from the scales of fruit belonging to *Daemonorops draco* Blume (family Palmaceae). It has been used medicinally as a stimulant and astringent, especially in dentifrices and mouth washes. Also it strongly inhibitd Lewis lung carcinoma (Tanka et. al, 1985).

Olaniyi et. al. (1973), Cardillo et. al. (1976), Agbakwuru and Whalley (1976) had worked with the separation, structural determination and synthesis of Dragon's Blood resin. Merlini and Nashini (1976) reported the resin in a rich source of some natural substances namly, flavans, biflavonoids, deoxyproanthocyanidins, triflavonoids, chalcones and terpenoids. Rao et. al. (1982) also found two compounds, dracorhodin and dracorubin from this plant and showed antimicrobial activity in vitro against *Staphylocossus aureus* and *Mycobacterium smegmatis*.

SUMMARY OF THE INVENTION

It is known from the above description that the prior studies of the Dragon's Blood resin are directed to the isolation of compounds used in medicine. Hitherto, no report has disclosed the isolation of compounds from the Dragon's Blood resin of *Daemonorops draco* Blume for use in agriculture. However, the inventors of the present invention now discovered that by specific isolating steps, a compound, 5-methoxy-7-hydroxyflavan can be obtained from the Dragon's Blood resin. This compound is an agriculturally safe and potent antifungal agent.

It is therefore an object of the present invention to provide an antifungal composition, comprising a compound of the formula (I):

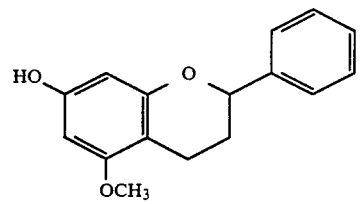

and an agriculturally acceptable carrier.

It is another object of the present invention to provide a method of preventing plants from the infection of the fungi, said method comprising applying an effective amount of compound (I) to the plants or the locus of the plants.

It is further an object of the present invention to provide a process for the isolation of compound (I) from Dragon's Blood resin, said process comprising the following steps:

(a) extracting Dragon's Blood with hexane, evaporating the hexane and leaving the defatted residue;
(b) extracting the defatted residue with ethanol:water (1:1) and leaving the ethanol fraction;
(c) partitioning the ethanol fraction between ethyl acetate and water and concentrating the ethyl acetate fraction;
(d) eluting the ethyl acetate fraction by silica gel chromatograph, using hexane, benzene and ethyl acetate as eluent to obtain the compound (I).

The above and other objects as well as the features and advantages of this invention can be more fully understood with respect to the examples in connection with the drawings, wherein:

DETAILED DESCRIPTION OF THE INVENTION

Figure 1:
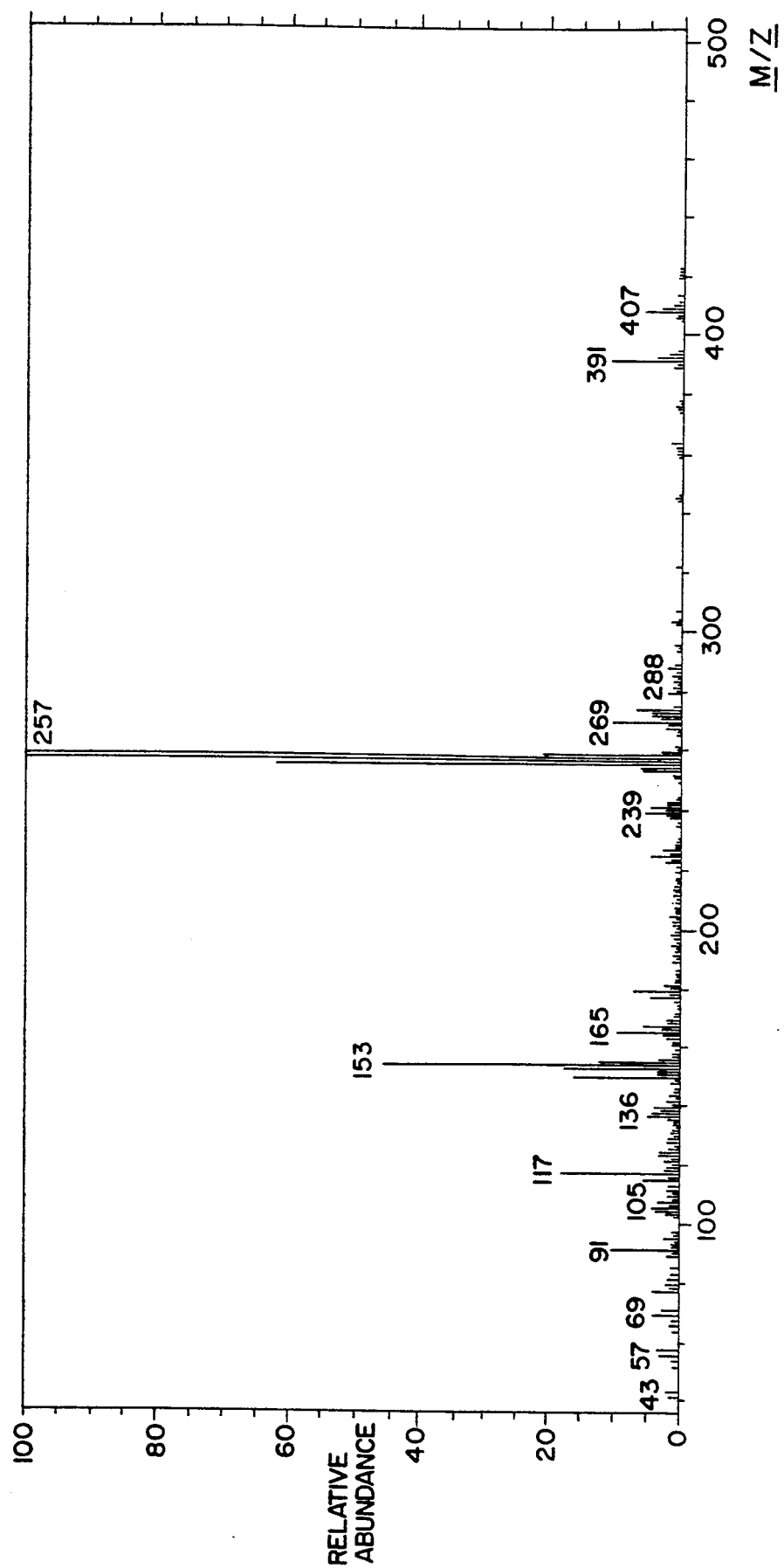
FIG. 1 is FAB-MASS Spectrum of compound (I)

In the below, the process for the isolation of compound (I) from the Dragon's Blood resin, the identification of compound (I) and the antifungal activity of the compound (I) on the plants is described by some examples. However, it is to be understood that these examples are only for description purpose, but not to be used as a limitation of the present invention. The scope of the present invention should be determined by the appended claims.

EXAMPLE 1

(Isolation of the compound (I))

The process of the isolation of compound (I) (5-methoxy-7-hydroxyflavan) from the Dragon's Blood resin is depicted in the following Scheme.

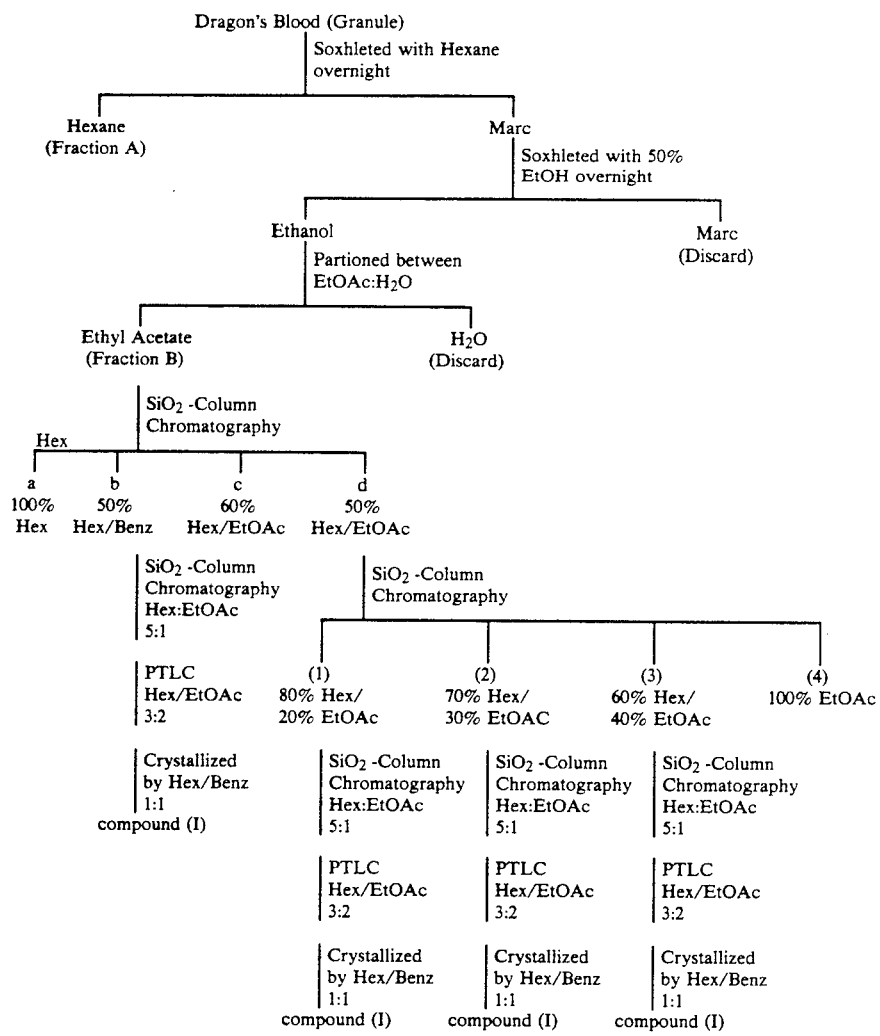

Dragon's blood (2.7 Kg) was extracted with n-hexane overnight. The n-hexane was then evaporated under vacuum. The defatted samples were soxhleted by ethanol:H$_2$O (1:1) overnight and evaporated by a rotary vacuum evaporator. Samples were partitioned between ethyl acetate(EtOAc) and water (H$_2$O). The EtOAc fraction was concentrated and loaded on a silica gel (35–70 mesh) column (6*60 cm) and eluted with n-hexane, benzene and EtOAc as depicted in Scheme 1. A quick in vitro assay against *Pythium spinosum* was made with fractions a to d. Fraction b,c, and d showed antifungal activity. The fractions b and c were absorbed on silica gel (70–230 mesh) and placed on top of a chromatographic column (2* 60 cm) of the same gel and eluted with hexane:EtOAc (5:1). The active fraction was purified by PTLC with hexane:EtOAc (3:2) and crystallized in benzene:hexane (1:1), and then compound (I) was obtained.

Fraction d was rechromatographed on silica gel (35–70 mesh) and eluted with n-hexane:EtOAc. The fraction d-(1), fraction d-(2) and fraction d-(3) were collected and loaded on a silica gel (70–230 mesh) column (2*60 cm) chromatograph separately and eluted with n-hexane:EtoAc (5:1). The amount of EtOAc was increased stepwisely to change the polarity of the elution solvent. The active fraction was obtained and purified by PTLC with hexane:EtOAc (3:2) and crystallized by hexane:benzene (1:1), and then compound (I) was obtained.

(Identification of compound (I))

The resulting compound (I) was isolated as a white needle-shaped crystal, m.p. 90° C., molecular weight 256, $[\alpha]_D^{25} = -5.85$ (C=0.002 g/ml in CHCl$_3$). Spraying the compound (I) on silica gel chromatoplate with Ehrlich's reagent shows a purple color, which is the characteristics of flavan. The elemental analysis of the resulting compound was as following:

$C_{16}H_{16}O_3$: Calculated C, 74.98, H, 6.29. Found C, 74.55, H, 6.34.

For further identification, acetylation of the resulting compound (0.98 g) was carried out by treatment with sodium acetate (0.3 g) and acetic anhydride (10 ml) on a steam bath for 2 hours. The reaction moisture was then evaporated to dryness and dissolved in acetone. Then ether was added to the solution to form the acetate of compound (I), which was then identified and found to be a compound having the structure of formula (II):

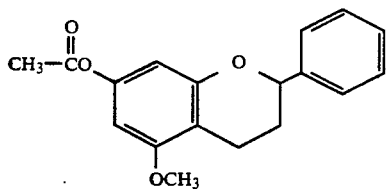

Acetylation of the compound (I) gave the monoacetate, $C_{18}H_{18}O_4$ (M/Z) indicating only one OH group in compound (I).

Figure 2:
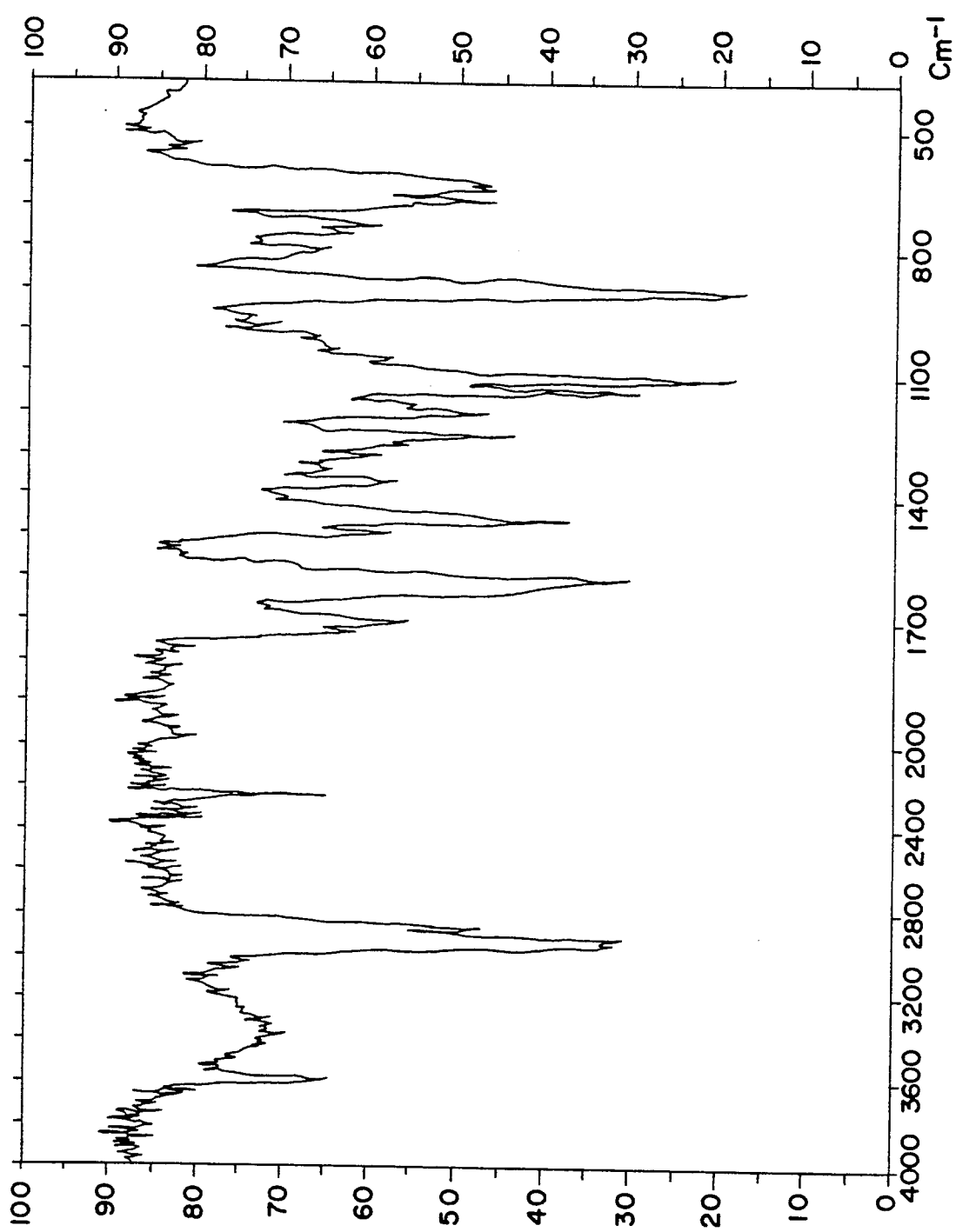
FIG. 2 is IR Spectrum of compound (I) in $CDCl_3$.
Figure 3:
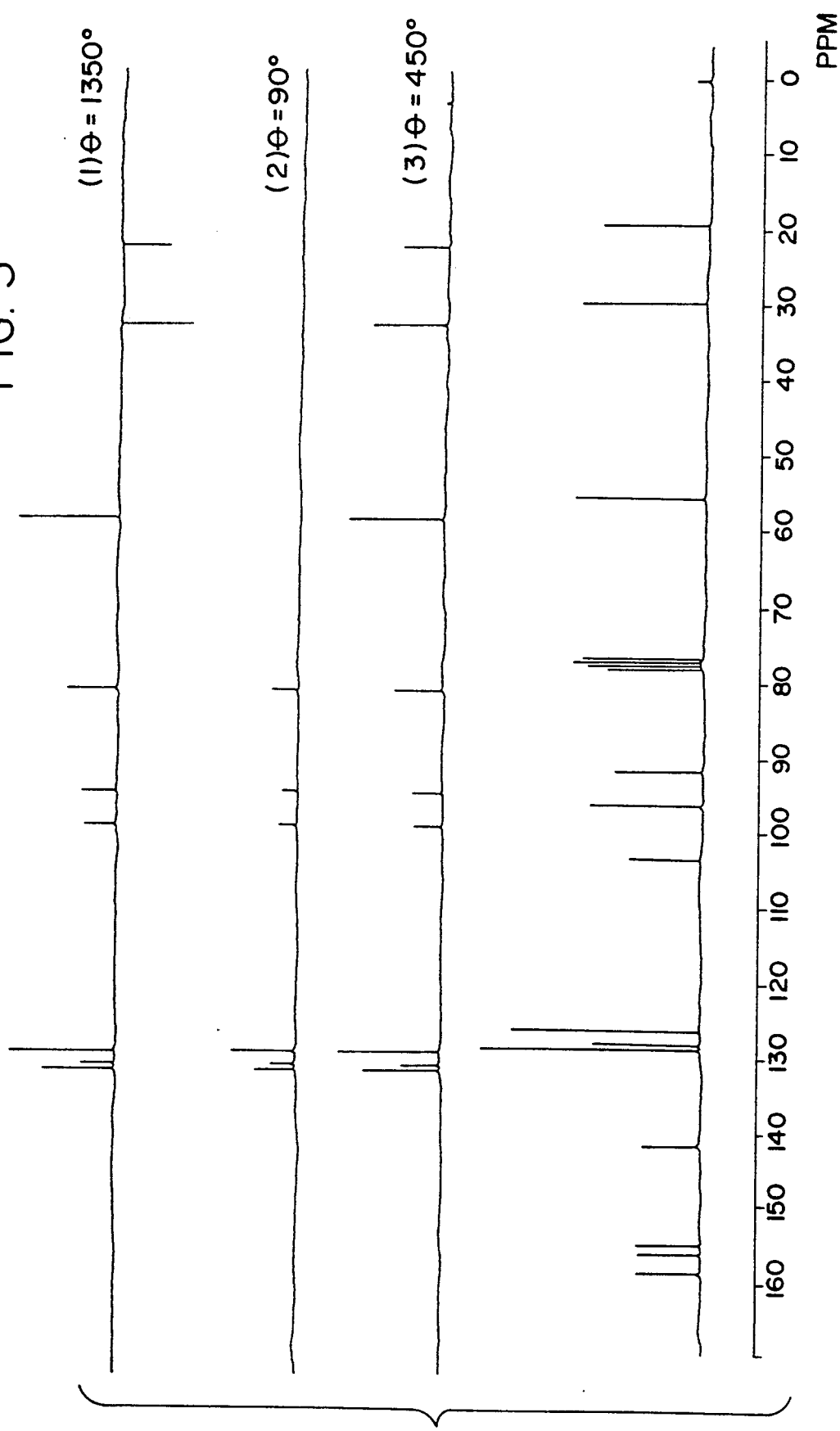
FIG. 3 is DEPT Spectrum of compound (I) in $CDCl_3$.
Figure 4:
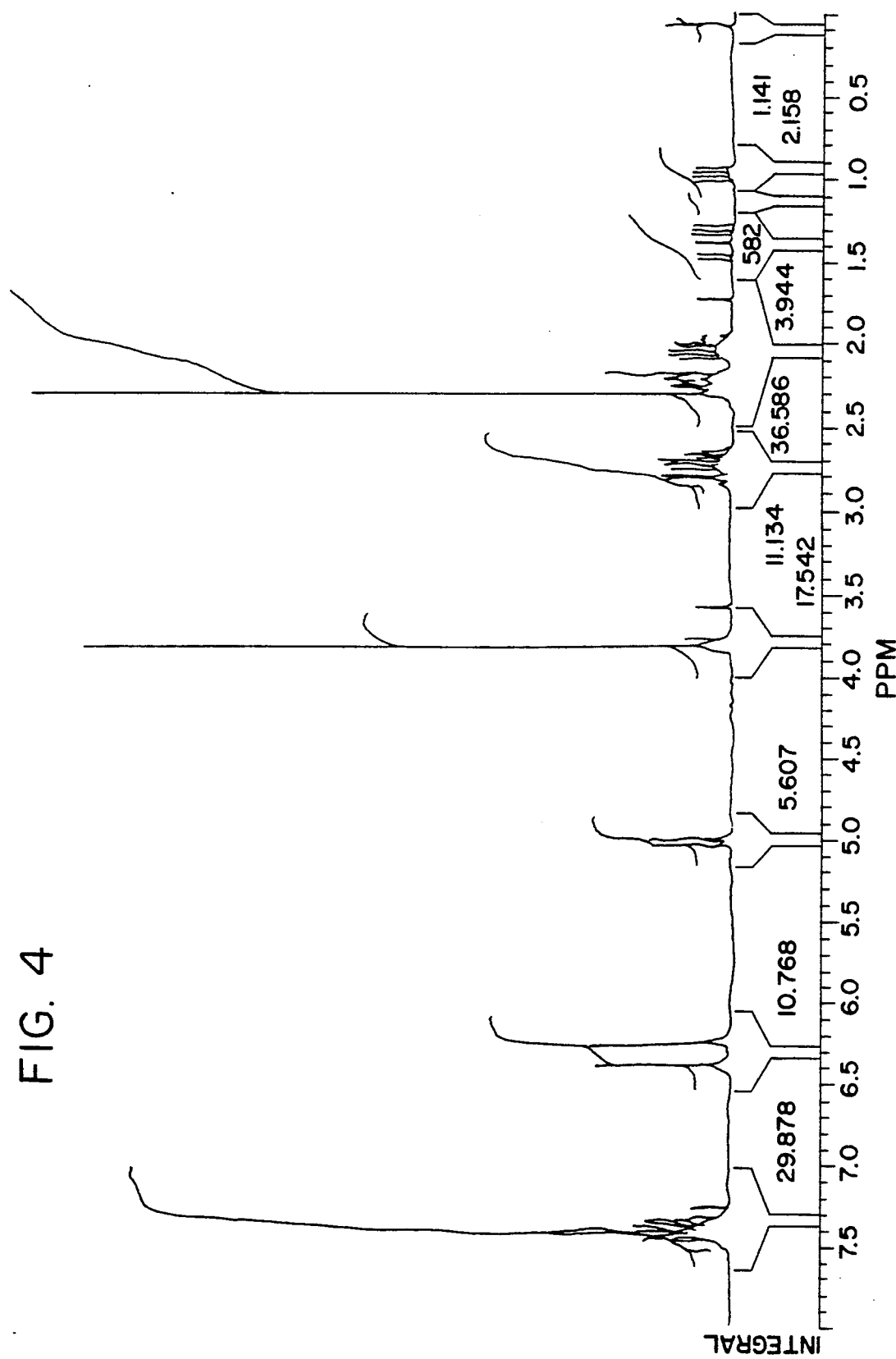
FIG. 4 is $^1$H-NMR Spectrum of compound (I) in $CDCl_3$ at 300 MHz.

Structures of both compound (I) and compound (II) were identified spectroscopically. Infrared (IR) spectra of both compound (I) and compound (II) were recorded on a Perkin-Elmer 882 infrared spectrophotometer. Fast Atom Bombardment (FAB)-Mass spectrum (Diethanol amine) and High Resolution Electron Impact (HREI)-Mass spectrum were determined by Jeol JMS-HX 110. NMR spectra and $^{13}$-$^1$H 2D Homonuclear Shift Correlation Experiment (COSY) were run with a Brucker AM-300 WB FT-NMR Spectrometer. TMS (in deuterized chloroform) was used as an internal standard for all samples analyzed in NMR. The above spectra data are shown in FIGS. 1-6. As shown in FIG. 1, the fragmentation pattern of FAB mass spectra of compound (I) was 257 (M+H)+, 256, 239, 177, 165(M-91)+, 152(M-104)+, 135, 124, 104 and 91. It revealed a flavan skeleton. The IR spectrum of the resulting compound in $CDCl_3$ is shown in FIG. 2. The $^{13}$C-NMR spectrum of the compound (I) was combined with DEPT studies (FIG. 3). It provided evidence for two methylenes (19.0, 29.3 ppm), one methine (77.6 ppm) and one methoxy carbon (55.3 ppm) as well as ten olefinic carbons. The $^1$H-NMR spectrum of compound (I) confirmed these general assignments. The above NMR spectra were shown in Table 1.

TABLE 1

| Assignment of carbon and hydrogen of compound (I) *and compound (II) by analysis between $^{13}$C-$^1$H2DCOSY and $^1$H NMR | | | | | |
|---|---|---|---|---|---|
| Carbon number | Signal (ppm) $^{13}$C-NMR | $^1$H-NMR | C.H. Assignment | | Proton |
| 3 | 19.0 | | 2.04(1H,m) 2.23(1H,m) | $CH_2<$ | 2H |
| 4 | 29.3 | | 2.78(2H,m) | $CH_2<$ | 2H |
| 17 | 55.3 | | 3.78(3H,s) | $CH_3$—O | 3H |
| 2 | 77.6 | | 5.01(1H,dd, J = 10.4, 2.2Hz) | | 1H |
| 6 | 91.3 | | 6.24(1H,d,J = 2.2Hz) | =CH | 1H |
| 8 | 96.0 | | 6.38(1H,d,J = 2.2Hz) | =CH | 1H |
| 10 | 103.3 | | | =C— | |
| 12-16 | 125.7 127.7 128.3 | | 7.33(5H,m) | =CH X2 =CH X1 =CH X2 | 5H |
| 11 | 141.4 | | | =C— | |
| 9 | 154.3 | | | =C— | |
| 5 | 156.1 | | | =C— | |
| 18 | 159.5 | | | =C— | |
| 19 | 21.9 | | 2.29(3H,S) | $CH_3$ | 3H |

*compound (I) is different from compound (II) by the carbon number 7 (substituting of carbon 19), the signal of $^1$H-NMR is 6.80 ppm (1H,br,s), shows one OH group and 1H.

Figure 5:
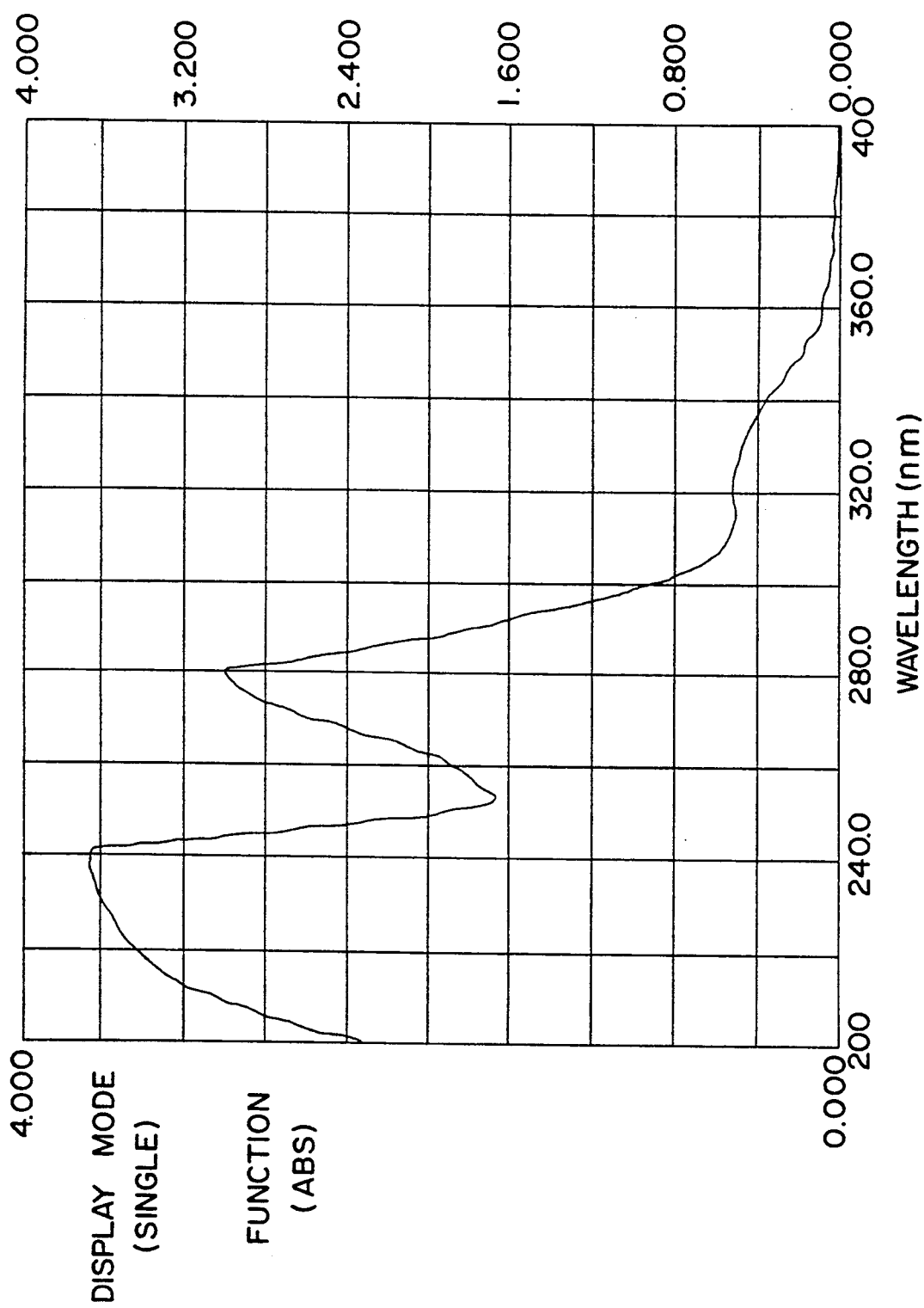
FIG. 5 is UV Spectrum of compound (I) in acetonitril.
Figure 6:
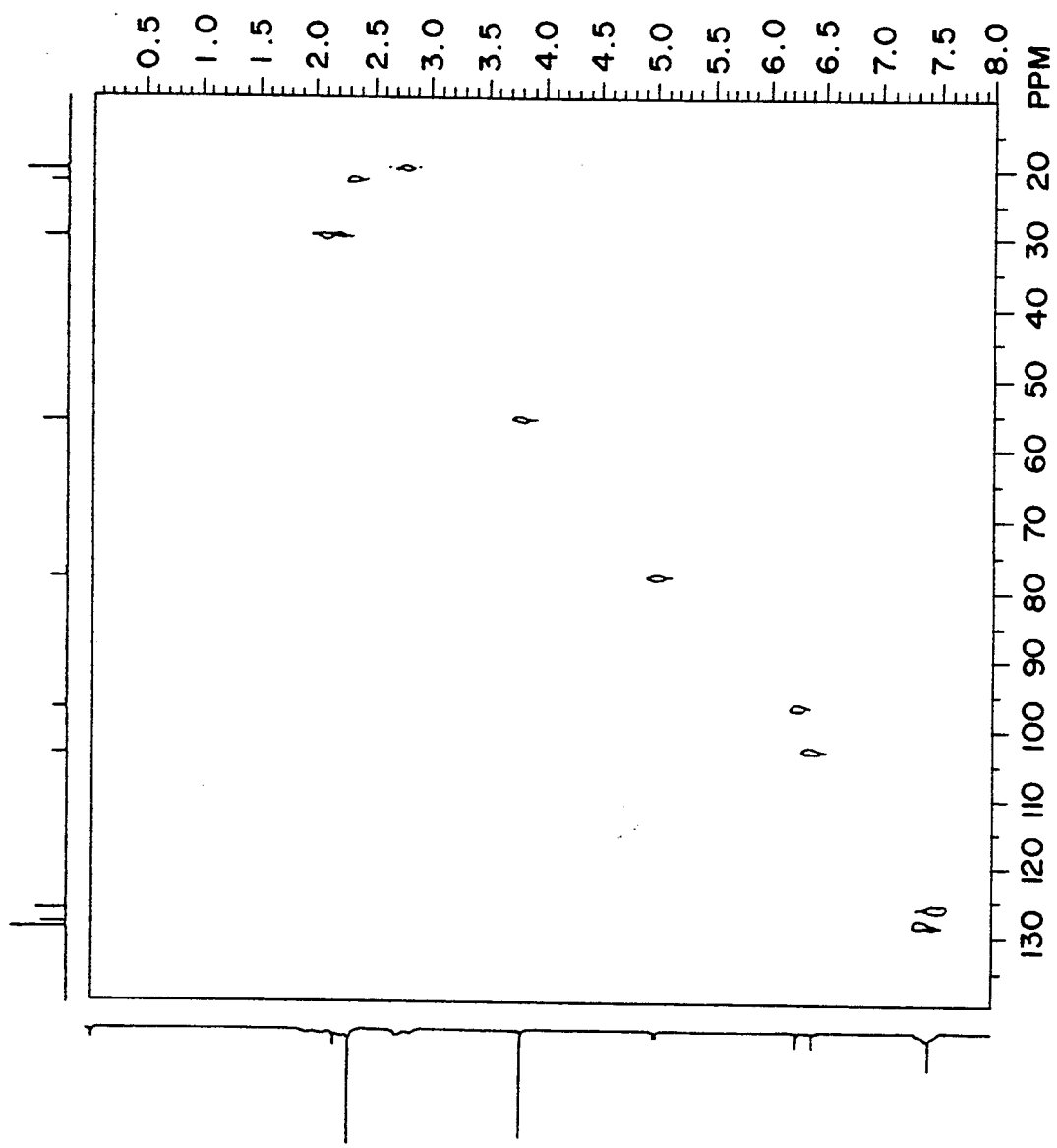
FIG. 6 is 2D COSY $^{13}$C-$^1$H correlation spectrum of compound (I).

FIG. 5 is the UV spectrum of compound (I) in acetonitrile. The UV spectrum consisted of two major absorption maxima, one of which occured at 238 nm while the other was less intense at 278 nm. The whole structure of compound (I) was finally proved by the $^{13}$C-$^1$H2D COSY technique. The $^{13}$C-$^1$H2D COSY spectrum was shown in FIG. 6.

In the following, the effect in inhibiting the growth of fungi is further proved by examples.

EXAMPLE 2

Minimum inhibitory concentration (MIC) in vitro

Compound (I) was dissolved in acetone and a sequential dilution (50% each time) was made to result in 13 different concentrations. Compound (I) of different concentration was added into glucose peptone media (glucose 20 g, yeast extract 2 g, $MgSO_4$ 0.5 g, $KH_2PO_4$ 5 g, polypeptone 1 g, and agar 15 g per liter) and placed in a 24-well plate. Four mm agar disc of 16 different species of fungi culture was placed on top of the media. Tests with each concentration of compound (I) and the individual fungi species were repeated 3 times. The tested culture was incubated at room temperature for 48 hours to record the radial growth of the fungal mycelium and the minimal concentration of inhibition exerted by compound (I) was determined. The results were shown in Table 2.

TABLE 2

| The minimal inhibitory concentration (MIC) of compound (I) on the target fungi | |
|---|---|
| Fungi | MIC (g/ml) |
| *Alternaria tenus* | >400 |
| *Aspergillus fumigatus* | 50 |
| *Aspergillus niger* | 50 |
| *Botrytis cinerea* | >400 |
| *Colletotrichum musae* | 400 |
| *Fusarium oxysporium* fsp. *niveum* | 100 |
| *Fusarium oxysporum* fsp. *cubense* | >400 |
| *Phoma asparagi* | 25 |
| *Phytophthora capsici* | 100 |
| *Pythium aphanidermatum* | 100 |
| *Pythium spinosum* | 50 |
| *Pythium sylvaticum* | 50 |
| *Rhizoctonia solani* AG 1 | 400 |
| *Rhizoctonia solani* AG 4 | >400 |
| *Sclerotium rolfsii* | 100 |
| *Sclerotinia sclerotiorum* | 100 |

It is seen from Table 2 that the compound (I) of the present invention is particularly potent in the inhibition of *Phoma asparagi, Pythium spinosum, pythium sylvaticum, Aspergillus fumigatus,* and *Aspergillus niger*. The MIC of compound (I) against the above fungi was less than 50 ug/ml. In contrast, compound (I) was slightly less active against *Sclerotium rolfsii* and *Sclerotinia sclerotiorum*.

EXAMPLE 3

In vivo whole plant evaluation tested in a growth chamber

The in vivo evaluation on the protection of whole plants from the fungal infection was performed with two sets of experiments. In the first set of experiments, mung bean (Vigna radiata (L.) cv. Wilczek) was chosen as plant material and the pathogen was *Sclerotium rolfsii*. The effect of compound (I) on the control of *S. rolfsii* was measured by mixing twenty pieces of sclerotia with 50 g of soil in a 4 inch pot and 10 ml of compound (I) of different concentrations (500 ppm or 1000 ppm) were mixed into the soil. After being cultured for 48 hours at room temperature, 10 mung bean seeds were planted in the pot. Each treatment included 4 replications. The experiments were conducted in a growth chamber set at 30° c. for 7 days. The germination rate of and survival rate were recorded at the third and seventh days of incubation. The results were shown in Table 3.

TABLE 3

Effects of compound (I) on the control of *Sclerotium rolfsii* infection on Mung bean

| Treatment | germination of Sclerotia (%) | Mung bean emergence (%) | survival (%) |
|---|---|---|---|
| compound (I) | | | |
| (1000 ppm) | 0 b* | 80.0 b | 70.0 b |
| (500 ppm) | 0 b | 72.5 b | 62.5 b |
| *CH 1 (distilled water) | 72.5 a | 2.5 c | 0 c |
| CK 2 (acetone) | 60.0 a | 5.0 c | 0 c |
| CK 3 (nonifested soil) | | 100.0 a | 100.0 a |

*The same letter indicated no significant difference at P = 0.05 level
*CK: control It is seen from the above table that the compound (I) of the present invention can significantly improve the emergence of the mung bean (>70%). In addition, the compound of the present invention can completely inhibit the germination of Scleotia. The survival of mung bean is also good.

In an another set of experiments, cabbage (*Brassica oleracea* cv. Capitata DC.) was selected as plant material and the pathogen was *Pythium aphanidermatum*. The pathogen was grown on potato dextrose broth for 3 days. The spores were washed out by distilled water and mixed with 3 ml mycelia plus 50 g of natural soil. The mixture was filled into a 4 inch pot. In each pot, 100 seeds of cabbage were planted and 10 ml of compound (I) (250 ppm or 500 ppm) was poured into the pot. The germination rate of cabbage seeds was recorded after 2 days of incubation. The results were shown in Table 4.

TABLE 4

Effects of compound (I) on the control of *Pythium aphanidermatum* infection on cabbage

| Treatment | Emergence(%) |
|---|---|
| compound (I) (500 ppm) | 59.6 a* |

TABLE 4-continued

Effects of compound (I) on the control of *Pythium aphanidermatum* infection on cabbage

| Treatment | Emergence(%) |
|---|---|
| (250 ppm) | 61.6 a* |
| *CK 1 (distilled water) | 32.6 b |
| *CK 2 (Acetone) | 28.0 b |
| CK 3 (noninfested soil) | 69.3 a |

*The same letter indicated no significant difference at P = 0.05 level by Ducan's Multiple Range Test.
*CK: control

EXAMPLE 4

Effects of compound (I) on the seed germination at various concentration

Seed germination tests were conducted with purified compound. The compound was diluted to various concentration. The effect of compound (I) on the seed germination was measured by mixing 70 g of soil and 10 ml of compound (I) at different concentrations. Thirty radish seeds, one hounderd cabbage seeds and one hounderd rape seeds were planted in each pot. Each treatment included 3 replications. Seed germination rate was recorded at 7 days after incubation in a growth chamber set at 24° C. The results were shown in Table 5.

TABLE 5

Effects of compound (I) on the seed germination at various concentration

| Treatment (ppm) | Germination rate (%) | | |
|---|---|---|---|
| | radish | cabbage | rape |
| 500 | 66.7 b* | 85.0 a | 79.0 a |
| 250 | 76.7 a | 86.3 a | 81.7 a |
| 125 | 75.6 ab | 85.7 a | 88.0 a |
| 62.5 | 72.2 ab | 87.3 a | 87.0 a |
| 31.5 | 75.6 ab | 86.3 a | 89.0 a |
| 15.6 | 75.6 ab | 84.7 a | 88.3 a |
| CK 1 (acetone) | 77.7 a | 85.7 a | 84.3 a |
| CK 2 (distilled water) | 73.3 ab | 84.0 a | 87.3 a |

*The same letter indicated no significant difference at P = 0.05 level by Duncan's Multiple Range Test.

In addition, toxicology experiments with compound (I) by Brion Research Institute of Taiwan showed no effect to animals dosed at 300 mg/kg perorally or 100 mg/kg intraperitoneally. From current test data, it appears that compound (I) is a safe and potent fungicide.

What is claimed is:

1. A method of preventing the infection of fungi in plants, said method comprising applying a fungicidally effective amount of the compound

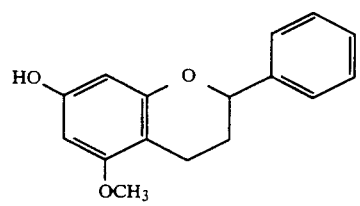

to the plants or the locus of the plants.

2. A method as claimed in claim 1, wherein said fungus is selected from the group consisting of *Phoma asparagi, Pythium spinosum, Pythium sylvaticum, Sclerotium rolfsii, Sclerotinia sclerotiorum* and *Aspergillus niger*.

* * * * *